(12) United States Patent
Doerr

(10) Patent No.: US 8,095,215 B2
(45) Date of Patent: Jan. 10, 2012

(54) MULTIPOLAR GUIDE WIRE AND ELECTRODE LINE

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 255 days.

(21) Appl. No.: 12/355,468

(22) Filed: Jan. 16, 2009

(65) Prior Publication Data

US 2009/0198313 A1    Aug. 6, 2009

(30) Foreign Application Priority Data

Feb. 5, 2008  (DE) .......................... 10 2008 007 542

(51) Int. Cl.
*A61N 1/00*    (2006.01)

(52) U.S. Cl. .................. 607/9; 607/4; 607/37; 607/115; 607/116

(58) Field of Classification Search .............. 607/4, 9, 607/37, 115–116
See application file for complete search history.

(56) References Cited

U.S. PATENT DOCUMENTS

| | | | | |
|---|---|---|---|---|
| 4,628,934 | A * | 12/1986 | Pohndorf et al. | ............... 607/27 |
| 5,325,870 | A | 7/1994 | Kroll | |
| 5,968,086 | A | 10/1999 | Bonner | |
| 6,418,348 | B1 | 7/2002 | Witte | |
| 6,859,667 | B2 | 2/2005 | Goode | |
| 2003/0149456 | A1 * | 8/2003 | Rottenberg et al. | ............. 607/37 |

FOREIGN PATENT DOCUMENTS

| | | |
|---|---|---|
| EP | 1 062 969 | 12/2000 |
| EP | 1 062 970 | 12/2000 |
| WO | WO 95/09561 | 4/1995 |
| WO | WO 2007/075974 | 7/2007 |

OTHER PUBLICATIONS

European Search Report, dated Jun. 23, 2009.
German Search Report, dated Nov. 17, 2008.

* cited by examiner

*Primary Examiner* — Niketa Patel
*Assistant Examiner* — Nicole F Lavert
(74) *Attorney, Agent, or Firm* — ARC IP Law, PC; Joseph J. Mayo

(57) ABSTRACT

Electrode arrangement for an electrical stimulation device, having electrode line (10) with electrical connection at proximal end of electrode line and with plurality of conductive surface areas (14, 16) in region of distal end of electrode line for emitting electrical pulses to a heart or for receiving electrical signals from the heart. Electrically conductive surface areas are at least partly electrically connected with the electrical connection at the proximal end of the electrode line. Uses switch or switching means (100), arranged within the electrical connection or within the electrode line, electrically arranged between at least one connection contact of the electrical connection and at least some of the electrically conductive surface areas (14b, 16), and which has an initially electrically conductive or non-conductive component (52), configured via a permanent configuration process by an electrical switching pulse to make permanently electrically non-conductive or conductive.

3 Claims, 6 Drawing Sheets

MULTIPOLAR GUIDE WIRE AND ELECTRODE LINE

This application takes priority from German Patent Application DE 10 2008 007 542.6, filed 5 Feb. 2008, the specification of which is hereby incorporated herein by reference.

BACKGROUND OF THE INVENTION

1. Field of the Invention

The invention relates to a guide wire for guiding and programming of electrode arrangements which can be inserted into human or animal bodies. Furthermore, the invention relates to a multipolar electrode arrangement for an electrical stimulation device such as, for example, an implantable heart pace maker, cardioverter/defibrillator, or the like.

2. Description of the Related Art

Such a guide wire comprises a longitudinal body with a proximal end which, after insertion of the guide wire, is located outside of a human or animal body, and a distal end which can be inserted into a body or into the lumen of an electrode line. It serves for guiding electrode arrangements safely to the treatment location. Also considered as a guide wire in the sense of the application is a mandrin, which is inserted into an electrode arrangement to actuate, for example, an active fixation.

An electrode arrangement according to the prior art has, at its proximal end, an electrical connection with electrical contacts for contacting the respective opposite contacts of a connection of the electrical stimulation device. At the distal end there are a plurality of electrically conductive surface areas, also referred to as poles, electrodes (e.g. ring or tip electrodes), or electrode poles, which are connected via corresponding feed lines with the electrical contacts of the connection of the electrode line.

Multipolar electrode lines which, e.g., are used for neurostimulation, have an adequately complex electrical connection in the form of an electrode connector comprising, e.g., 8 contacts. Furthermore, the number of practicable electrode poles is limited by the number of possible electrode feed lines.

For the application of the cardial stimulation (e.g. coronary sinus electrodes for the cardial resynchronization therapy), the multipolar electrodes could not establish themselves so far because the current connector standards (IS-1, in the future IS-4) do not support the use of multipolar electrodes.

For the final application, when using multipolar electrode lines, only some of the available electrode poles are utilized. The selection of the same happens either by means of electrical inspection after implantation or already before the implantation based on the anatomical conditions.

U.S. Pat. No. 6,859,667 describes the integration of a multiplexer in an electrode with the goal to remain compatible to the actual connector standards. Here, however, a permanent active control of the multiplexer by means of the electronic implant is required. The disadvantage of this known solution is that an implant, which is adapted to the electrode and its multiplexer, is required at all times.

In U.S. Pat. No. 6,418,348, a multiplexer integrated into the distal end of the electrode is described as well. Here, it is also required that the electronic implant carries out the electrode configuration, and hence an appropriate connector configuration and device configuration is necessary. The connection of this electrode to conventional electronic implants is not possible.

From EP 1 062 970, an electrode line is known which, between a central feed line and a respective electrode pole, comprises electronic or mechanical switching means by means of which an electrode pole can be permanently connected with the central feed line or can be permanently disconnected from the central feed line so that, as a result, only some selected electrode poles are connected via the feed line with the electrical contacts of the connection of the electrode line for the output of stimulation pulses or the reception of electrical potentials.

U.S. Pat. No. 4,628,934 shows an electrode line in the electrical connection of which (e.g. the electrode connector) or in the electrode feed line (preferably at the distal end of the electrode line) of which one-time electrically programmable switching means are integrated, which can be configured by an external device by means of an electronic configuration process before or after the implantation in such a manner that each of the contacts of the electrical connection of the electrode line are subsequently allocated to one or more of the electrode poles of the electrode line. Hence, by means of the one-time electrically programmable switching means, at completion of the configuration process, it is defined, permanently and without the need of further energy, which electrode poles are connected in an electrically conductive manner with which contact of the electrical connection of the electrode line, and which are not.

The disadvantage of this solution is that the implant can not be structured as a standard because additional control means are to be provided, which are necessary for the programming of the lines.

BRIEF SUMMARY OF THE INVENTION

It is hence an object to further develop a "programmable" electrode arrangement in such a manner that it can be used in a simple and easy manner with standard implants. The object is solved as claimed herein in such a manner that the electrode line has a lumen for inserting a guide wire which is provided with electrical contacts which are connected to electrical switching means so that the electrical switching means are to be controlled by means of a guide wire provided with electrical opposite contacts when such a guide wire is inserted into the lumen.

Thus, the required electrical connection for the "programming" before the connection of the electrode line to an electronic implant can be completely eliminated and, for example, no additional control lines need to be provided by means of which, according to the prior art, the "programming" takes place. Preferably, for the electrical connection, which is required for the "programming", between multiplexer, the electrically permanent configurable switching means, and the programming and test device, a guide wire (mandrin) designed for this purpose is to be provided. For this, the electrode line preferably has a lumen for inserting such a guide wire which is provided with electrical contacts which are connected with the multiplexer so that the multiplexer is to be controlled by means of a mandrin provided with electrical opposite contacts when such a mandrin is inserted into the lumen.

For this, the configuration takes place by means of non-reversible electronic or electrical components as switching means, e.g., by means of safety devices (fuses) or by electronic components such as Zener diodes (Zener zapping), wherein by means of the one-time programming, either an existing electrical connection is permanently disconnected (blowing of a fuse) or a blocked semiconductor connection is made permanently conductive (e.g. by Zener zapping).

The advantages of this solution, on the one hand, are the possibility to link a multipolar electrode to current connector standards (e.g. IS-1, in the future IS-4). Here, most notably to mention are the advantages with respect to the compatibility between electrodes and devices of different manufacturers as well as the aspects of reliability (less contact points).

Furthermore, when integrated into the electrode tip, this technology allows the development of multipolar electrodes with considerably more electrode poles while the number of electrode lines remains constant or increases insignificantly only, and hence the diameter of the electrode remains unchanged compared to conventional multipolar electrodes.

According to a preferred variant of an embodiment, a multiplexer is integrated into the electrode line in such a manner that the electrode poles are to be selectively connected before the permanent configuration with a respective contact of the connection to be able to test the electrode configuration first. The multiplexer integrated into the electrode line hence serves for the determination of a suitable electrode combination and allows adjusting the possible electrode configuration temporarily before the permanent configuration (programming) of the electrode.

The temporary configuration of the electrode can take place here by means of an external "programming and test device". This "programming and test device" includes all functions for testing a respective electrode configuration as well as the control of the multiplexer for the temporary testing and the programming device for the permanent configuration (programming) of the electrode line.

A further object is to be able to carry out the described "programming" of the electrode arrangement without complex additional functions in the implant or in the electrode arrangement itself.

For this, the guide wire of the prior art is further developed in such a manner that it has, at the distal end, at least one electrically conductive contact which is connected by means of at least one line in a electrically conductive manner with the proximal end and which is formed to contact electrical switching means of an electrode line.

In this manner, the programming is made easier and the electrode line can be utilized with conventional implants which do not need to have additional switching or programming means. In addition, the structure of the electrode line can be kept simple this way, which results in a diameter reduction due to less electrical lines.

According to a specific embodiment, the guide wire has, at the proximal end, an electrical connection which is connected with the contacts by means of the electrical line and which is formed to be connected with an external test and programming device. Thus, the "programming" is further simplified for the user because by means of this advantageously standardized connection, an erroneous programming is prevented.

According to a further embodiment, the at least one electrical line is guided insulated within or on the guide wire.

BRIEF DESCRIPTION OF THE DRAWINGS

The invention is now explained in more detail by means of exemplary embodiments with reference to the figures. In the figures.

DETAILED DESCRIPTION OF THE INVENTION

Figure 1:
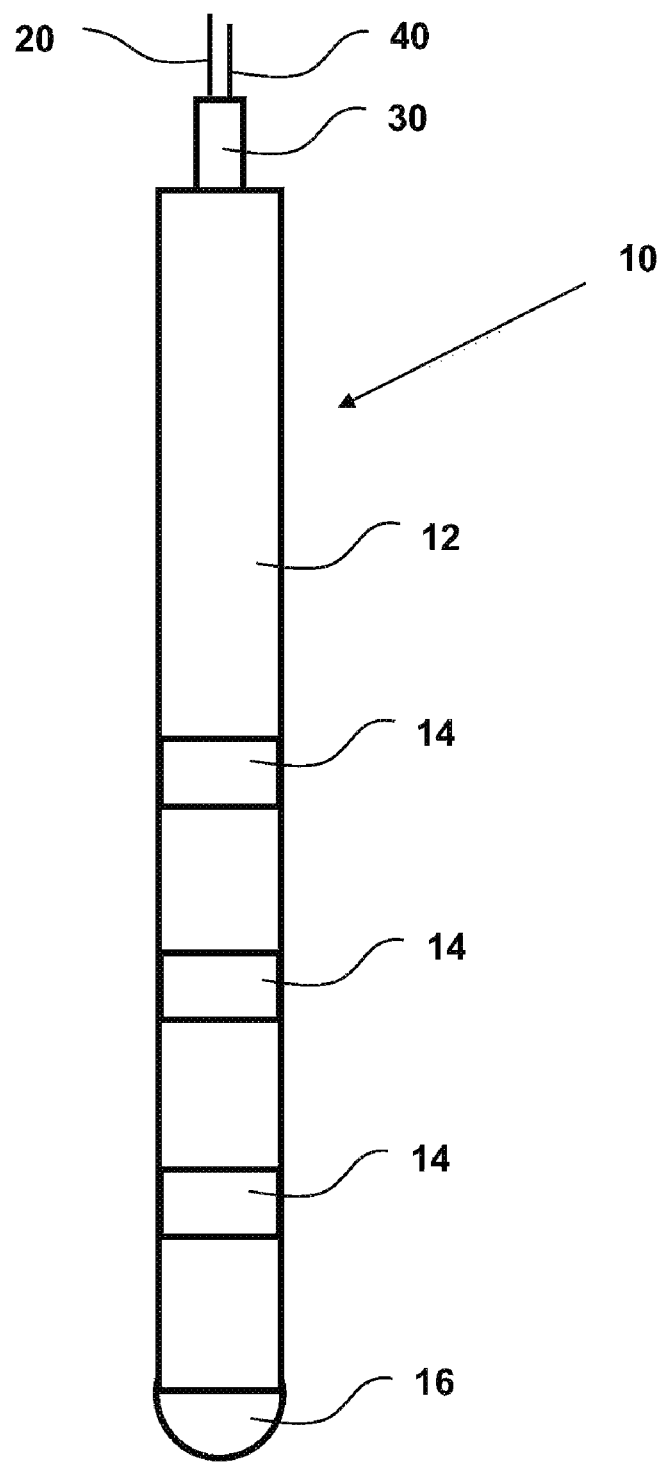
FIG. 1 shows a distal end of a multipolar electrode line.

As shown in the schematic illustration of a distal end of a multipolar electrode line 10 in FIG. 1, the multipolar electrode line has an electrode line 12 in the strict sense, which has a plurality of electrically conductive surface areas as electrode poles, namely ring electrodes 14, on the one hand, and a chip electrode or tip electrode 16 on the other hand. In order to electrically connect the electrode poles 14 and 16 with electrical contacts of an electrical connection, which is not shown in FIG. 1, at the proximal end of the electrode line 10, inside the electrode line 12, electrical feed lines 20, 30, and 40 are provided, the feed lines 20 and 40 of which have the form of a simple wire, while the electrical feed line 30 has the form of a wire coil which encloses a lumen inside. The electrical feed lines 20 and 40 can be arranged outside or inside the lumen of the wire coil forming the electrical feed line 30.

Between at least some of the electrode poles 14 and 16 and at least some of the electrical feed lines 20, 30, or 40, according to the invention, a switching means is arranged to selectively permanently connect a respective electrode pole electrically with an electrical feed line or to disconnect it therefrom. This is explained hereinafter with reference to the FIGS. 2a, 2b, and 3 in more detail.

Figure 2A:
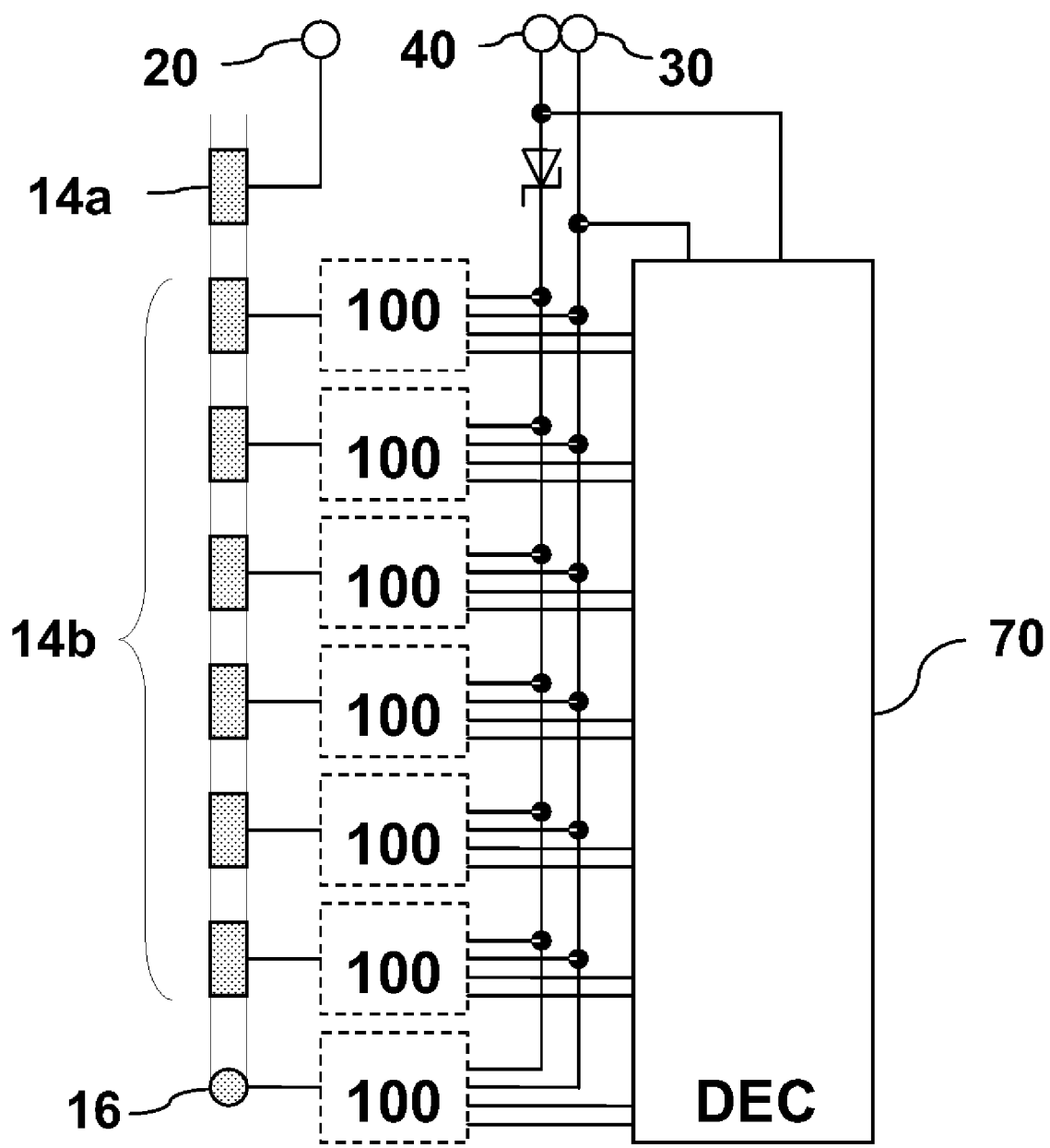
FIG. 2a shows a block diagram of a first variant of a multipolar electrode line.

FIG. 2a shows the block diagram of a multipolar electrode with a fixed electrode pole 14a, which is electrically fixed connected with an electrical contact of an electrical connection of the electrode line by means of the feed line 20, and with seven programmable electrode poles 14b, 16, each of which is connected with a second feed line 30 by means of an electrical switching means 100, which serves as a "programming unit" and which is explained hereinafter in more detail with reference to FIG. 3. The electrical switching means 100, in turn, is connected with a multiplexer 70, the common electrode feed line 30, and an electrical feed line 40 which serves as a "programming line". Such a multipolar electrode line 10 is suitable, e.g., as a coronary sinus electrode line with an electronically "shiftable" ring electrode for cardial resynchronization therapy.

In fact, with the aid of the multiplexer 70, a respective electrical switching means 100 can be controlled in such a manner that it connects the respectively allocated electrode 14b or 16 with the electrical feed lines 30 or it disconnects it therefrom. As explained hereinafter in more detail with reference to FIG. 3, this can happen first temporarily to connect, for example, on a test base, each of the electrode poles 14b, respectively, with a contact of the connection at the proximal end of the electrode line. By consistently connecting a different electrode pole 14b with the feed line 30, this results in a quasi wandering ring electrode. Subsequently, the electrical connection between a respective electrode pole 14b and the feed line 30 can be established permanently or can be disabled permanently.

Figure 2B:
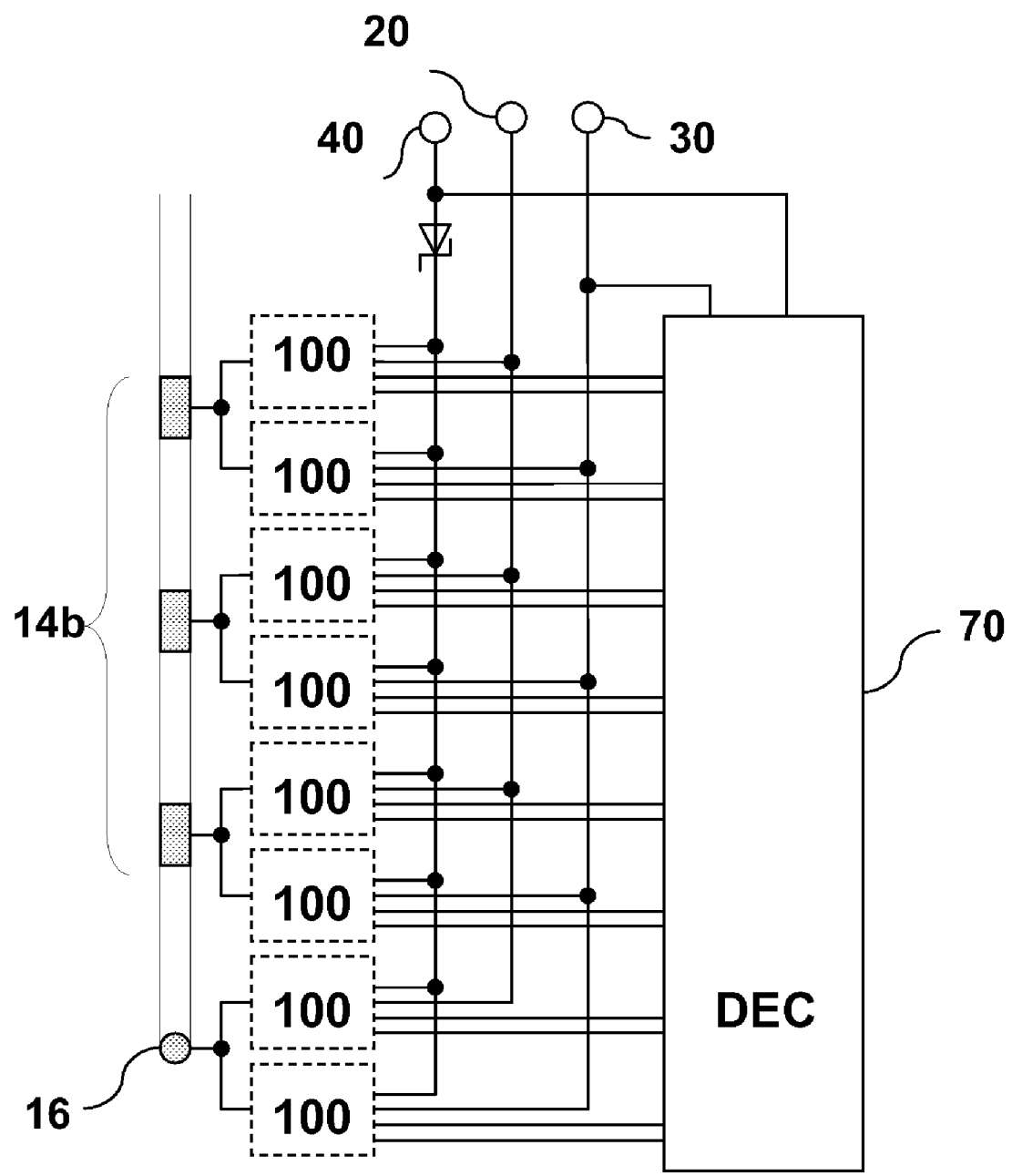
FIG. 2b shows a block diagram of a second variant of a multipolar electrode line.

FIG. 2b shows the block diagram of a 4-fold multipolar electrode line, of which none of the poles is fixed connected with a contact of the electrical connection of the electrode line. Rather, each of the electrode poles 14b or 16 can be selectively permanently connected in an electrical manner by means of the feed line 30 or the feed line 40 with the one or the other contact of, for example, an electrode line connector according to the IS-1 Standard. For this purpose, the "programming unit" 100 shown in FIG. 3 is available twice for each of the electrode poles 14b or 16, and is, in each case, connected with one of the two common electrode feed lines 20 or 30, and the "programming line" 40. Such an arrangement can be used, for example, in the neurostimulation for spinal cord stimulation.

A multiplication as desired of the multiplexer structure allows the construction of electrodes with more than 2 common electrode lines such as, for example, an electrode with 8 connector contacts and, e.g., 16 or 32 freely configurable electrode poles.

Figure 3:
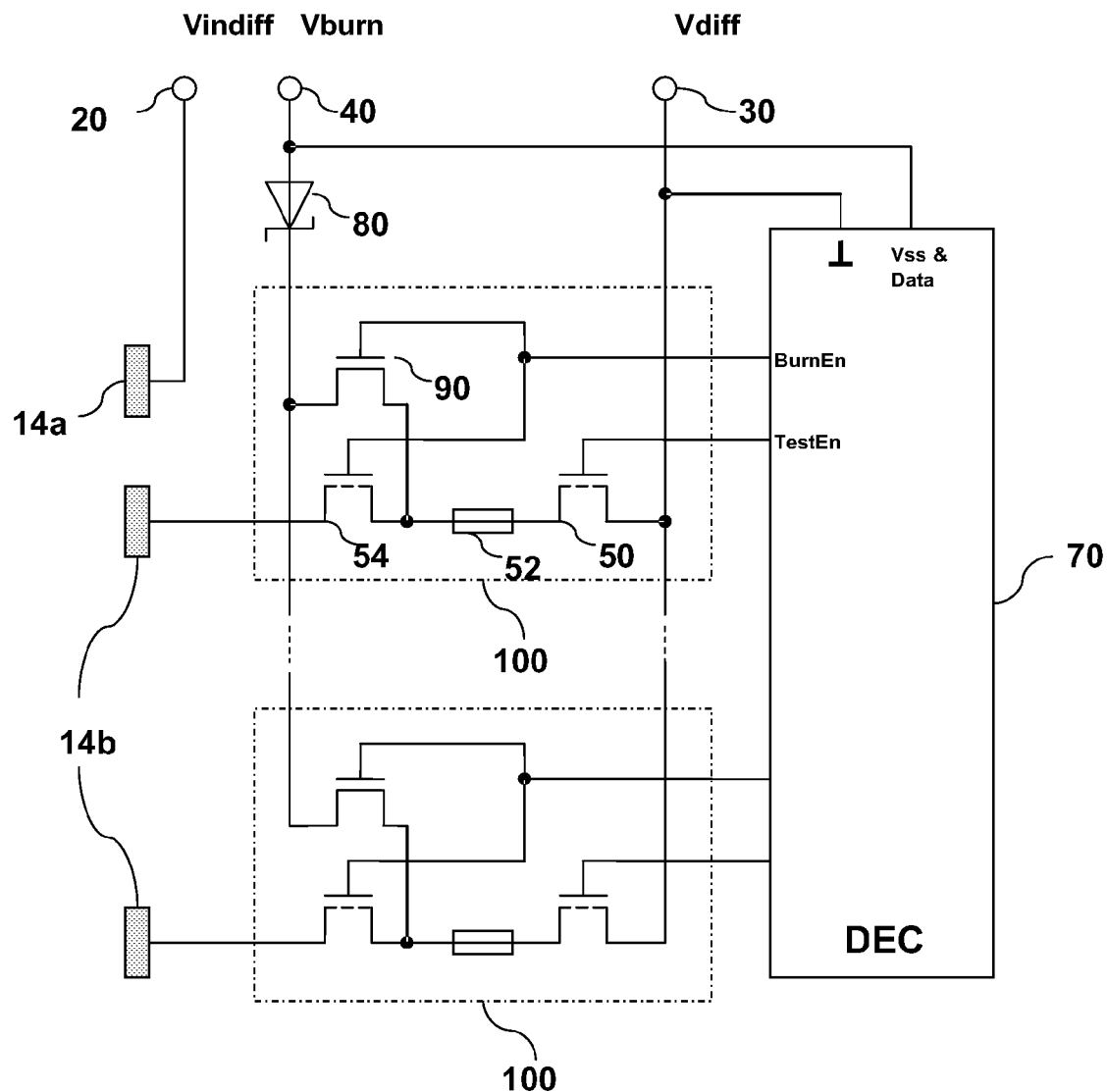
FIG. 3 shows a switching means for the permanent configuration of an individual electrode pole for an electrode line according to FIG. 2a or FIG. 2b.

FIG. 3 shows a possible switching means for a permanent configuration of an individual electrode pole. First, a common feed line 30 is connected with a plurality of electrode poles. This feed line 30 is in each case connected with the electrode pole 14b to be selected by means of a first MOS transistor [depletion type] 50, a fuse 52, and a second MOS transistor [depletion type] 54. Due to the used depletion type of MOS transistors, thus at first all electrode poles 14b are connected with the common feed line 30.

For a permanent "programming" of an electrode pole, via the additional electrode feed line 40, a current is supplied which blows the fuse 52 so that the electrode pole programmed in this manner is permanently disconnected from the common line 30. The selection of the electrode pole to be "programmed" takes place here by means of a multiplexer 70 as a decoder, which receives its voltage supply by means of the additional electrode feed line 40, tapped upstream of a Z diode 80, and the common electrode feed line 30. The control of the multiplexer 70 takes place by means of a signal which is modulated onto the voltage supply so that additional control lines can be eliminated. For the permanent programming, a respective electrode pole 14b to be programmed is selected by the multiplexer 70 by means of the signal BurnEn. The signal opens a transistor 90 and blocks the transistor 54 to prevent a current output into the tissue during the "programming process". At the same time, the voltage in the feed line 40 is increased in such a manner that the threshold voltage of the Z diode 80 is exceeded and the fuse 52 is blown. With this process, the permanent disconnection (programming) of one or more electrode poles is completed.

For the temporary testing, the output TestEn is available for the multiplexer 70. By means of this signal, for temporary tests, one or more electrode poles can be disconnected from the common electrode line 30 by blocking the depletion mode MOS transistor 50.

For the complete overview, the active electrode pole 14a and its feed line 20 is also shown in this implementation example, wherein the feed line is always hard-wired in this example.

Figure 4:
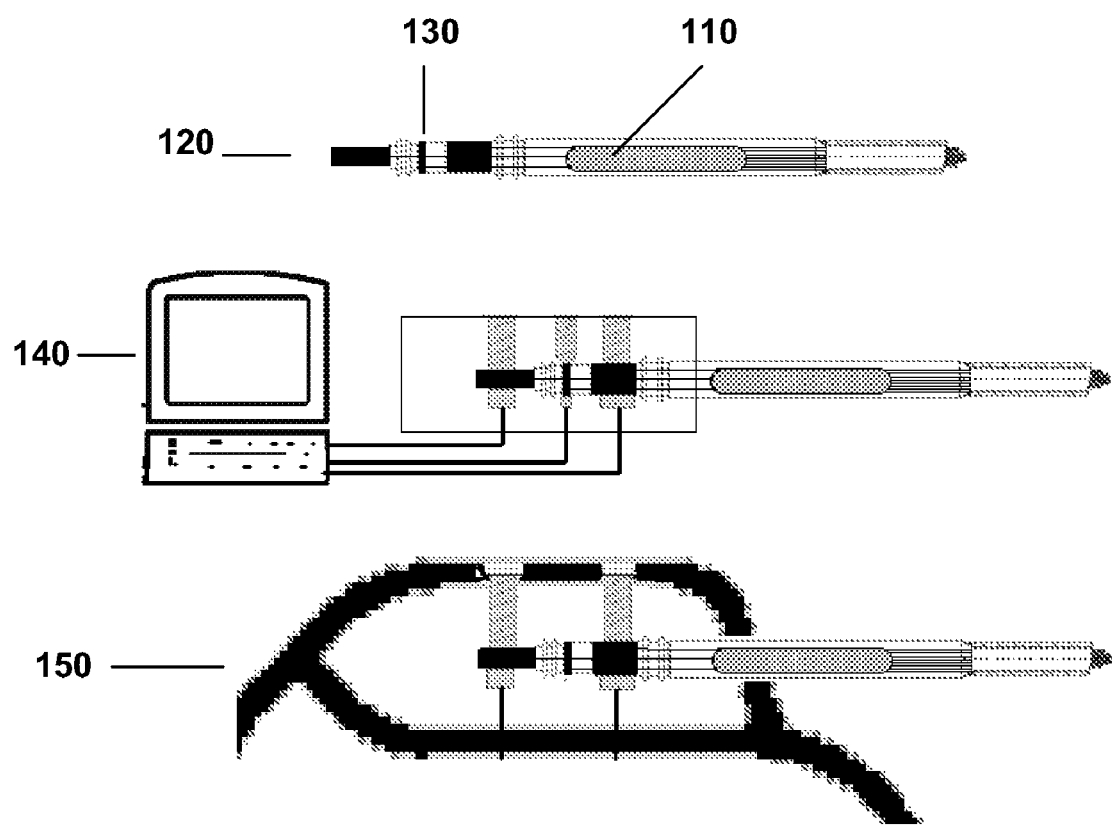
FIG. 4 shows an electrode line comprising a multichip module integrated into an electrode line connector.

In FIG. 4, the integration of a multichip module 110 for the permanent electrode programming into a bipolar connection 120 at the proximal end of the electrode line 10 according to the IS-1 Standard is shown. The contact 130 of the feed line 40 for the programming is arranged here in such a manner that the contact is exclusively contacted by an external test and programming device 140 and remains insulated during the connection of the electrode line 10 with the electronic implant 150.

Figure 5:
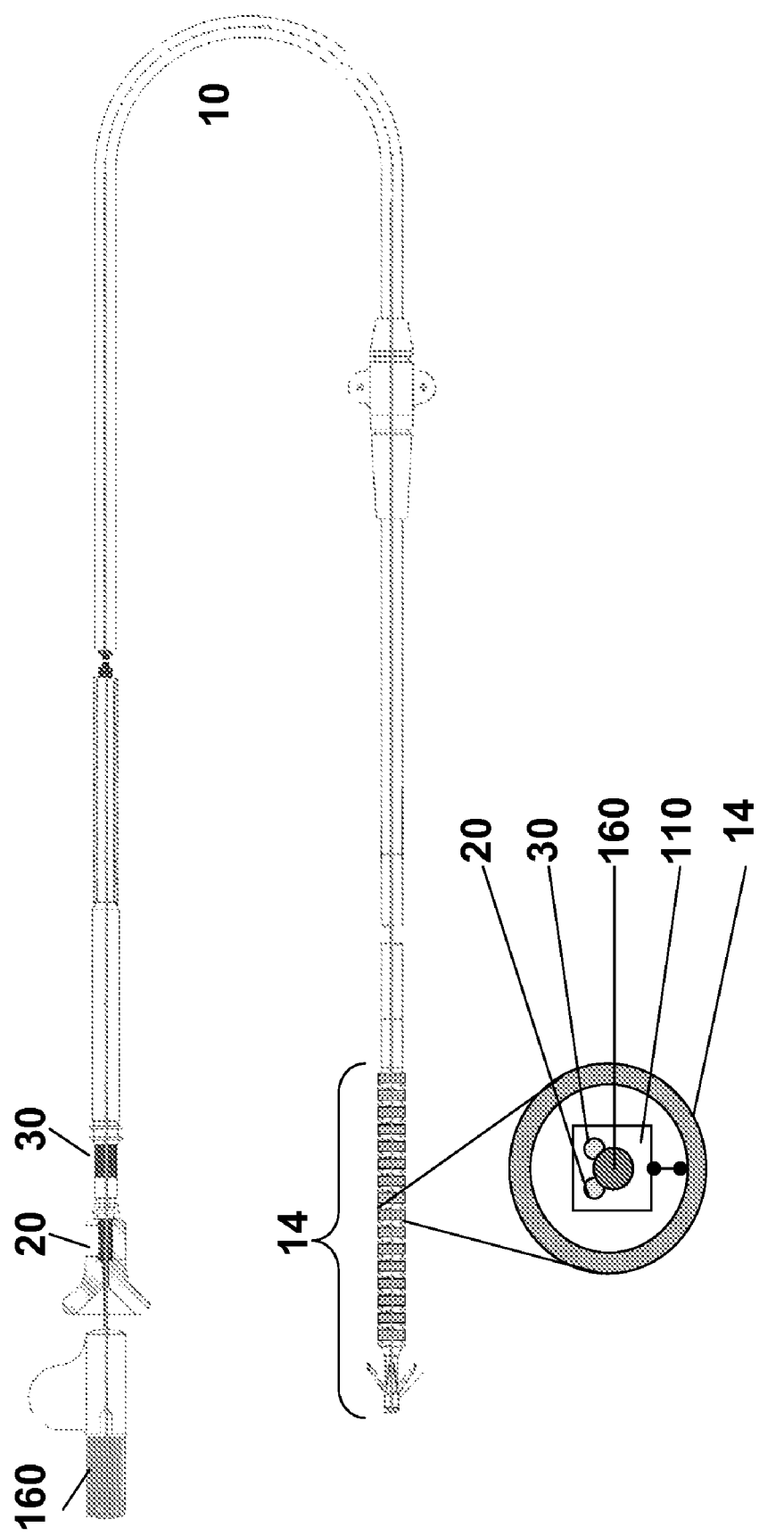
FIG. 5 shows an electrode line comprising a plurality of multichip modules arranged in the region of the distal end of the electrode line.

FIG. 5 shows an electrode line 10 with a plurality of multichip modules 110 which are integrated in the region of the electrode poles 14 into the electrode line 10. The electrical connection of these multichip modules 110 with an external test and programming device 140 takes place in this case with a guide wire 160 which is specifically developed for this purpose and which, for configuration of the electrode line 10, is electrically connected with its proximal end with the external test and programming device 140, and, with the appropriate electrical contacts at its distal end, contacts the multichip modules 110. This guide wire is removed before the connection of the electrode line 10 to the electronic implant 150. For this, the electrode line 10 has a lumen in which the guide wire 160 is to be inserted and which, in the region of the multichip modules 110, has electrical contacts which are electrically connected with the multichip modules 110.

Further illustrated in a cross section is the permanent connection of the multichip module of an electrode pole with the two electrode feed lines 20 and 30.

What is claimed is:

1. An electrode arrangement for an electrical stimulation device comprising:
   an electrode line (10) comprising an electrical connection (120) at a proximal end of the electrode line;
   a plurality of conductive surface areas (14, 16) in a region of a distal end of the electrode line wherein the plurality of conductive surface areas are configured to emit electrical pulses to a heart or to receive electrical signals from the heart;
   wherein the plurality of conductive surface areas are at least partly electrically connected with the electrical connection at the proximal end of the electrode line;
   an electrical switch (100), arranged within the electrical connection (120) or within the electrode line (10);
   wherein the electrical switch is electrically arranged between at least one connection contact of the electrical connection and, in each case, at least some of the plurality of conductive surface areas (14b, 16);
   wherein the electrical switch has an initially electrically conductive or non-conductive component (52), which, is formed into a permanent configuration by an electrical pulse, that thus configures the initially electrically conductive or non-conductive component (52) into a permanently electrically non-conductive or conductive configuration, respectively, so that a respectively allocated conductive surface selected from said the plurality of conductive surface areas (14b, 16) is subsequently permanently connected with a respective connection contact selected from the at least one connection contact of the electrical connection or is permanently electrically disconnected with a connection contact;
   wherein the electrical connection (120) at the proximal end of the electrode line (10) comprises two contacts and has an additional third contact (130), which is connected with a feed line (40) that is configured to be utilized as a programming line of the electrode line (10);
   wherein within the electrode line (10), a multiplexer (70) is integrated in such a manner that selectable electrically conductive surfaces are selectively connected before the configuration process with a respective contact of the electrical connection of the electrode line;
   wherein the electrical connection (120) is configured to be connected with an external test and programming device (140) to non-permanently connect said electrical connection to at least one of said plurality of conductive surface areas and to finally permanently connect said electrical connection to desired conductive surfaces areas; and,
   wherein said additional third contact (130) is not connected to said electrical stimulation device after said electrode line is coupled with said electrical stimulation device and wherein said electrical stimulation device comprises no multiplexer control lines.

2. The electrode arrangement according to claim 1, wherein each of the initially electrically non-conductive components comprises a Zener diode.

3. An electrode arrangement for an electrical stimulation device comprising:
- an electrode line (10) comprising a first electrical connection (20) and a second electrical connection (30) at a proximal end of the electrode line;
- a plurality of conductive surface areas (14, 16) in a region of a distal end of the electrode line wherein the plurality of conductive surface areas are configured to emit electrical pulses to a heart or to receive electrical signals from the heart;
- wherein the plurality of conductive surface areas are at least partly electrically connected with the electrical connection at the proximal end of the electrode line;
- an electrical switch (100), arranged within the electrode line (10);
- wherein the electrical switch is electrically arranged between at least one connection contact of the electrical connection and, in each case, at least some of the plurality of conductive surface areas (14*b*, 16);
- wherein the electrical switch has an initially electrically conductive or non-conductive component (52), which, is formed into a permanent configuration by an electrical pulse, that thus configures the initially electrically conductive or non-conductive component (52) into a permanently electrically non-conductive or conductive configuration, respectively, so that a respectively allocated conductive surface selected from said the plurality of conductive surface areas (14*b*, 16) is subsequently permanently connected with a respective connection contact selected from the at least one connection contact of the electrical connection or is permanently electrically disconnected with a connection contact;
- wherein the electrode line has a lumen configured to insert a guide wire (160), which is provided with electrical contacts which are connected with the electrical switch (100) so that the electrical switch (100) is controlled by the guide wire (160) when the guide wire (160) is inserted into the lumen and wherein said guide wire (160) is removed from said lumen when said electrode line is coupled with said electrical stimulation device;
- wherein the guide wire (160), at the proximal end, has an electrical connection which is connected by an electrical line with contacts and which is formed to be connected with an external test and programming device (140); and,
- wherein said first electrical connection (20) and said second electrical connection (30) may contact any of said plurality of conductive surface areas temporarily or permanently once programmed by said external test and programming device (140) via said guide wire and wherein no other wires besides any wires coupled with said first electrical connection (20) and said second electrical connection (30) respectively exist in said electrode line for the purpose of electrical conduction between said first electrical connection (20), said second electrical connection (30) and programmed conductive surface areas.

* * * * *